(12) United States Patent
Brown et al.

(10) Patent No.: US 6,838,468 B2
(45) Date of Patent: Jan. 4, 2005

(54) 4-(PHENYL-PIPERDIN-4-YLIDENE METHYL)-BENZAMIDE DERIVATIVES AND THEIR USE FOR THE TREATMENT OF PAIN, ANXIETY OR GASTROINTESTINAL DISORDERS

(75) Inventors: William Brown, Montreal (CA); Christopher Walpole, Montreal (CA); Zhongyong Wei, Montreal (CA)

(73) Assignee: AstraZeneca AB, Sodertalje (SE)

( * ) Notice: Subject to any disclaimer, the term of this patent is extended or adjusted under 35 U.S.C. 154(b) by 8 days.

(21) Appl. No.: 10/477,641

(22) PCT Filed: May 16, 2002

(86) PCT No.: PCT/SE02/00947

§ 371 (c)(1),
(2), (4) Date: Nov. 13, 2003

(87) PCT Pub. No.: WO02/094811

PCT Pub. Date: Nov. 28, 2002

(65) Prior Publication Data

US 2004/0147553 A1 Jul. 29, 2004

(30) Foreign Application Priority Data

May 18, 2001 (SE) .............................. 0101768

(51) Int. Cl.[7] ...................... A61K 31/47; C07D 215/12; C07D 211/32
(52) U.S. Cl. ........................ 514/314; 546/176; 546/233
(58) Field of Search ......................... 514/314; 546/176, 546/233

(56) References Cited

U.S. PATENT DOCUMENTS

| 2,898,339 | A | 8/1959 | Wheeler et al. |
| 4,581,171 | A | 4/1986 | Kennis et al. |
| 4,816,586 | A | 3/1989 | Portoghese |
| 4,939,137 | A | 7/1990 | Russell et al. |
| 5,140,029 | A | 8/1992 | Kennis et al. |
| 5,574,159 | A | 11/1996 | Chang et al. |
| 5,683,998 | A | 11/1997 | Shibayama et al. |
| 6,187,792 | B1 | 2/2001 | Delorme et al. |
| 6,455,545 | B2 | 9/2002 | Delorme et al. |

FOREIGN PATENT DOCUMENTS

| WO | WO 93/15062 | 8/1993 |
| WO | WO 97/23466 | 7/1997 |
| WO | WO 98/28275 | 7/1998 |
| WO | WO 99/33806 | 7/1999 |
| WO | WO 0174804 | 10/2001 |
| WO | WO 0174806 | 10/2001 |
| WO | WO 2002094811 | * 11/2002 |

OTHER PUBLICATIONS

Bilsky, et al., SNC 80, A Selective, Nonpeptidic and Systemically Active Opioid Delta Agonist, J. Pharmacol. Experi. Ther. 273:359–366(1995).
Takemori, et al., "Selective Natrexone–Drived Opioid Receptor Antagonists," Annu. Rev. Pharmacol. Toxicol. 32:239–269 (1992).
Barber, et al., "Antinociceptive Effects of the 5–HT Antagonist Ritanserin in Rats: Evidence for an Activation . . . in the Spinal Cord," Neuroscience Letters 99:234–238 (1989).
Greene, "Protective Groups in Organic Synthesis," Wiley & sons, pp. 218, 220, 232, 233, 251 (1982).
Wei, et al., "N,N–Diethyl–4–(phenylpiperidin–4–ylidenemethyl) . . . and its Analogues," J. Med. Chem. 43:3895–3905 (2000).
Zhang, et al., "Probes for Narcotic Receptor Mediated Phenomena. 26. 1–3 Synthesis . . . Opioid Receptor Ligands," J. Med. Chem. 42:5455–5463 (1999).

* cited by examiner

Primary Examiner—D. Margaret Seaman
(74) Attorney, Agent, or Firm—Jianzhong Shen

(57) ABSTRACT

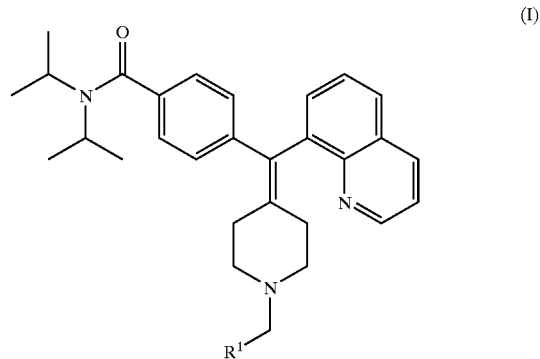

(I)

Compounds of general formula I[Chemical formula should be inserted here. Please see paper copy] $R_1$ is selected from any one of phenyl, pyridinyl, pyrrolyl, thienyl, furanyl, imidazolyl, triazolyl, and pyridine N-oxide; where each $R_1$ phenyl ring and $R_1$ heteroaromatic ring may optionally and independently be further substituted by 1,2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems; are disclosed and claimed in the present application, as well as their pharmaceutically acceptable salts and pharmaceutical compositions comprising the novel compounds and their use in therapy, in particular in the management of pain, anxiety and functional gastrointestinal disorders.

11 Claims, No Drawings

4-(PHENYL-PIPERDIN-4-YLIDENE METHYL)-BENZAMIDE DERIVATIVES AND THEIR USE FOR THE TREATMENT OF PAIN, ANXIETY OR GASTROINTESTINAL DISORDERS

CROSS-REFERENCE TO RELATED APPLICATIONS

This application is a U.S. National Stage of International Application No. PCT/SE02/00947 that was filed on May 16, 2002. The International Application claims priority under 35 U.S.C. §119(a) to Swedish Application No. 0101768-0 filed May 18, 2001.

FIELD OF THE INVENTION

The present invention is directed to novel compounds, to a process for their preparation, their use and pharmaceutical compositions comprising the novel compounds. The novel compounds are useful in therapy, and in particular for the treatment of pain, anxiety and functional gastrointestinal disorders.

BACKGROUND OF THE INVENTION

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors ($\mu$, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., *Journal of Pharmacology and Experimental Therapeutics*, 273(1), pp. 359–366 (1995)). There is however still a need for selective δ-agonists having not only improved selectivity, but also an improved side-effect profile.

Thus, the problem underlying the present invention was to find new analgesics having improved analgesic effects, but also with an improved side-effect profile over current $\mu$ agonists, as well as having improved systemic efficacy.

Analgesics that have been identified and are existing in the prior art have many disadvantages in that they suffer from poor pharmacokinetics and are not analgesic when administered by systemic routes. Also, it has been documented that preferred δ agonist compounds, described within the prior art, show significant convulsive effects when administered systemically.

We have now found certain compounds that exhibit surprisingly improved properties, i.a. improved δ-agonist potency, in vivo potency, pharmacokinetic, bioavailability, in vitro stability and/or lower toxicity.

Outline of the Invention

The novel compounds according to the present invention are defined by the formula I

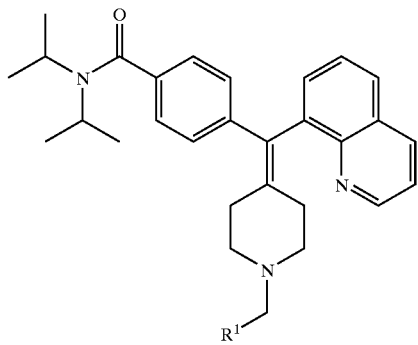

wherein $R^1$ is selected from any one of (i) phenyl;

(ii) pyridinyl

(iii) thienyl

(iv) furanyl

(v) imidazolyl

(vi) triazolyl

(vii) pyrrolyl,

(viii) thiazolyl

(ix) pyridyl-N-oxide

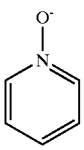

where each $R^1$ phenyl ring and $R^1$ heteroaromatic ring may optionally and independently be further substituted by 1, 2 or 3 substituents independently selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems;

A further embodiment of the present invention is a compound according to FIG. I wherein $R^1$ is as defined above and each $R^1$ phenyl ring and $R^1$ heteroaromatic ring may independently be further substituted by a methyl group A further embodiment of the present invention is a compound according to FIG. I wherein $R^1$ is phenyl, pyrrolyl, pyridinyl, thienyl or furanyl, optionally with 1 or 2 of the preferred substituents on the $R^1$ phenyl or $R^1$ heteroaromatic ring.

Another embodiment of the present invention is a compound according to FIG. I wherein $R^1$ is phenyl, pyrrolyl or pyridinyl, optionally with 1 or 2 of the preferred substituents on the $R^1$ phenyl or $R^1$ heteroaromatic ring.

Another embodiment of the present invention is a compound according to FIG. I wherein $R^1$ is thienyl or furanyl, optionally with 1 or 2 of the preferred substituents on the $R^1$ heteroaromatic ring.

Within the scope of the invention are also salts and enantiomers of the compounds of the formula I.

When the $R^1$ phenyl ring and the $R^1$ heteroaromatic ring(s) are substituted, the preferred substituents are independently selected from any one of $CF_3$, methyl, iodo, bromo, fluoro and chloro.

Reaction step A in Scheme 2, vide infra, is performed by reacting an intermediate compound of the general formula II

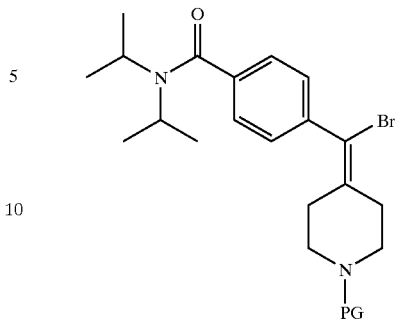

II wherein PG is a urethane protecting group such as Boc or CBZ, or a benzyl or a substituted benzyl protecting group, such as 2,4-dimethoxybenzyl, with 8-quinoline boronic acid, using a palladium catalyst, e.g. $Pd(PPh_3)_4$, in the presence of a base, e.g. $Na_2CO_3$, to give the compounds of general formula III,

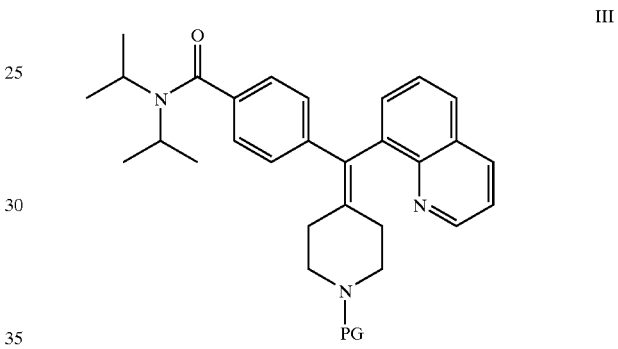

III which is thereafter deprotected, under standard conditions and alkylated using either:
i) a compound of the general formula $R^1$—$CH_2$—X, wherein $R^1$ is as defined above and X is a halogen, preferably bromine or chlorine and a suitable base, or
ii) a compound of the general formula $R^1$—CHO, wherein $R^1$ is as defined above, and a suitable reducing agent, to give compounds of the general formula I.

Suitable bases to be used in the standard alkylation step i) above include, but are not limited to, triethylamine and potassium carbonate.

Suitable reducing agents to be used in the standard reduction step ii) include, but are not limited to, sodium cyanoborohydride and sodium triacetoxyborohydride.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety and stress-related disorders such as post-traumatic stress disorders, panic disorder, generalized anxiety disorder, social phobia, and obesessive compulsive disorder; urinary incontinence, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

A further aspect of the present invention is intermediates of the general formula II and III, wherein PG is a urethane protecting group such as Boc or CBZ, or a benzyl or a substituted benzyl protecting group, such as 2,4-dimethoxybenzyl.

Methods of Preparation

EXAMPLES

The invention will now be described in more detail by the following Examples, which are not to be construed as limiting the invention.

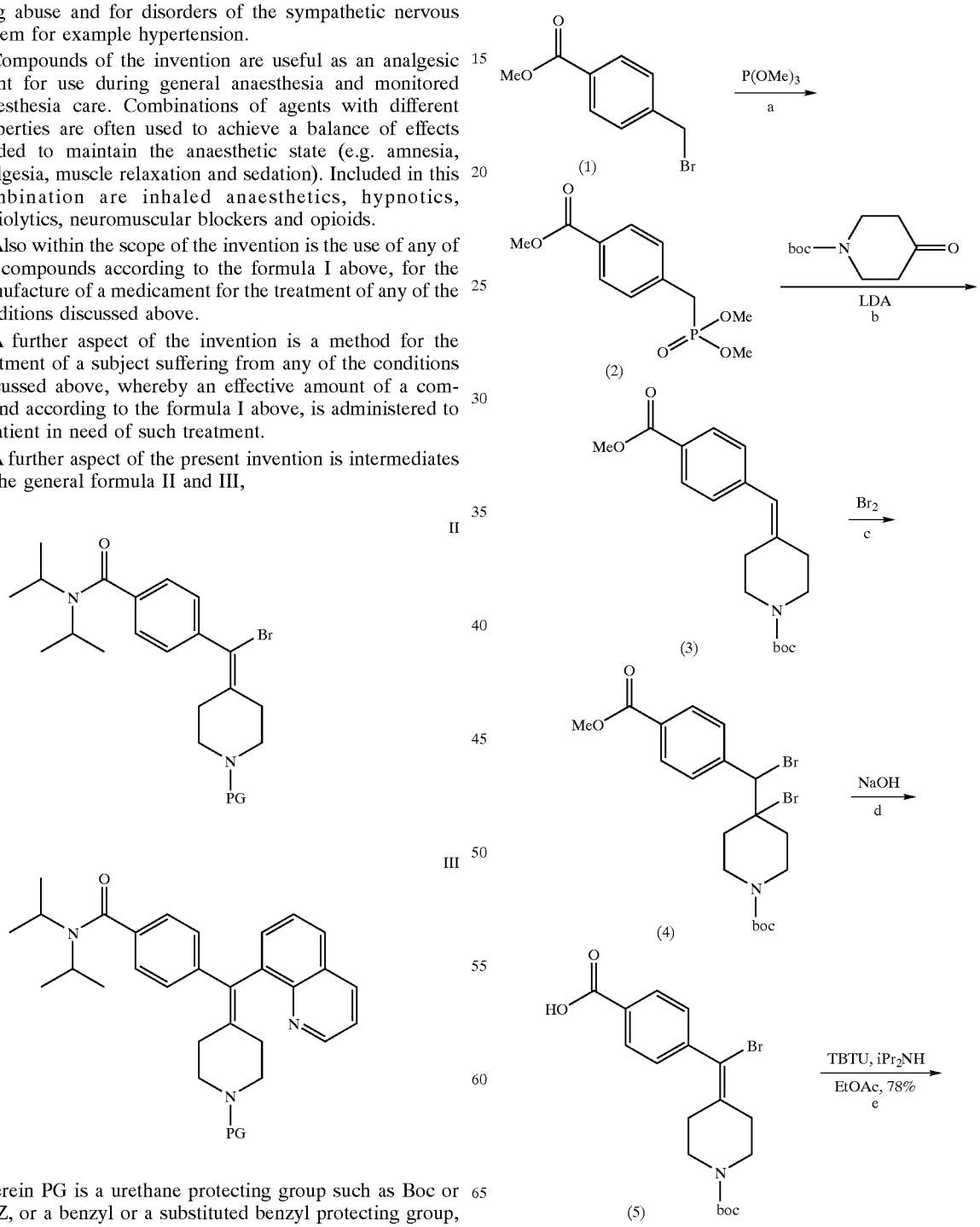

Scheme 1
Synthesis of vinyl bromide intermediate 6

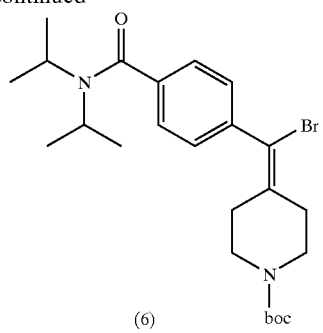

(6)

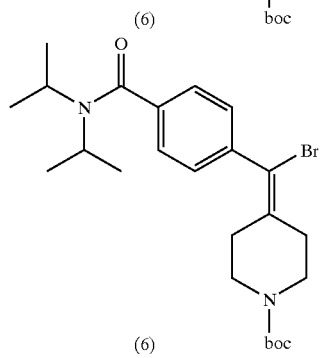

(6)

Intermediate 2: 4-(Dimethoxy-phosphorylmethyl)-benzoic acid methyl ester

A mixture of starting material 1 (11.2 g, 49 mmol) and trimethyl phosphite (25 mL) was refluxed under $N_2$ for 5 hrs. Excess trimethyl phosphite was removed by co-distillation with toluene to give compound 2 in quantitative yield:

$^1$H NMR(CDCl$_3$) δ 3.20 (d, 2H, J=22 Hz), 3.68 (d, 3H 10.8 Hz), 3.78 (d, 3H, 11.2 Hz), 3.91 (s, 3H), 7.38 (m, 2H), 8.00 (d, 2H, J=8 Hz).

Intermediate 3: 4-(t-Methoxycarbonyl-benzylidene)-piperidine-1-carboxylic acid tert-butyl ester To a solution of 2 in dry THF (200 mL) was added dropwise lithium diisopropylamide (32.7 mL 1.5 M in hexanes, 49 mmol) at −78° C. The reaction mixture was then allowed to warm to room temperature prior to addition of N-tert-butoxycarbonyl-4-piperidone (9.76 g, 49 mmol in 100 mL dry THF). After 12 hrs, the reaction mixture was quenched with water (300 mL) and extracted with ethyl acetate (3×300 mL). The combined organic phases were dried over MgSO$_4$ and evaporated to give a crude product, which was purified by flash to provide 3 as a white solid (5.64 g, 35%):

IR (NaCl) 3424, 2974, 2855, 1718, 1 688, 1606, 1427, 1362, 1276 cm$^{-1}$; $^1$H NMR (CDCl$_3$) δ 1.44 (s, 1H), 2.31 (t, J=5.5 Hz, 2H), 2.42 (t, J=5.5 Hz, 2H), 3.37 (t, J=5.5 Hz, 2H), 3.48 (t, J=5.5 Hz, 2H), 3.87(s, 3H), 6.33 (s, 1H), 7.20 (d J=6.7 Hz, 2H), 7.94 (d, J,=6.7 Hz, 2H); $^{13}$C NMR (CDCl$_3$) δ 28.3, 29.2, 36.19, 51.9, 123.7, 127.8, 128.7, 129.4, 140.5, 142.1, 154.6, 166.8.

Intermediate 4: 4-Bromo-4-[bromo-(4-methoxycarbonyl-phenyl)-methyl]-piperidine-1-carboxylic acid tert-butyl ester To a mixture of 3 (5.2 g, 16 mmol) and $K_2CO_3$ (1.0 g) in dry dichloromethane (200 mL) was added a solution of bromine (2.9 g, 18 mmol) in 30 mL CH$_2$Cl$_2$ at 0° C. after 1.5 hrs at room temperature, the solution after filtration of $K_2CO_3$ was condensed. The residue was then dissolved in ethyl acetate (200 mL), washed with water (200 mL), 0.5 M HCl (200 mL) and brine (200 mL), and dried over MgSO$_4$. Removal of solvents provided a crude product, which was recrystallized from methanol to give 4 as a white solid (6.07 g, 78%):

IR (NaCl) 3425, 2969, 1725, 1669, 1426, 1365, 1279, 1243 cm$^{-1}$; $^1$H NMR (CDCl$_3$) δ 1.28 (s, 9H), 1.75 (m, 1H), 1.90 (m, 1H), 2.1 (m, 2H), 3.08 (br, 2H), 3.90 (s, 3H, OCH$_3$), 4.08 (br, 3H, 7.57 (d, J=8.4 Hz, 2H, Ar—H) 7.98 (d, J=8.4 Hz, 2H, Ar—H); $^{13}$C NMR (CDCl$_3$) δ 28.3, 36.6, 38.3, 40.3, 52.1, 63.2, 72.9, 129.0, 130.3, 130.4, 141.9, 154.4, 166.3.

Intermediate 5: 4-[bromo-(4-carboxy-phenyl)-methylene]-piperidine-1-carboxylic acid tert-butyl ester A solution of 4 (5.4 g 11 mmol) in methanol (300 mL) and 2.0 M NaOH (100 mL) was heated at 40° C. for 3 hrs. The solid was collected by filtration, and dried overnight under vacuum. The dry salt was dissolved in 40% acetonitrile/water, and was adjusted to pH 2 using concentrated HCl. Product 5 (3.8 g, 87%) was isolated as a white powder by filtration:

$^1$H NMR (CDCl$_3$) δ 1.45 (s, 9H, $^t$Bu), 2.22 (dd, J=5.5 Hz, 6.1 Hz, 2H), 2.64 (dd, J=5.5 Hz, 6.1 Hz, 2H), 3.34 (dd, J=5.5 Hz, 6.1 Hz, 2H), 3.54 (dd, J=5.5 Hz, 6.1 Hz, 2H), 7.35 (d, J=6.7 Hz, 2H, Ar—H), 8.08 (d, J=6.7 Hz, 2H, Ar—H); $^{13}$C NMR (CDCl$_3$) δ 28.3, 31.5, 34.2, 44.0, 115.3, 128.7, 129.4, 130.2, 137.7, 145.2, 154.6, 170.3.

Intermediate 6: 4-[bromo-(4-diisopropylcarbamoyl-phenyl)-methylene]-piperidine-1-carboxylic acid tert-butyl ester To a light suspension of acid (5) (50.27 g, 0.127 mol, 1.0 equiv.) in ethyl acetate (350 ml) at room temperature is added diisopropylamine (71.10 mL, 0.510 mol, 4.0 equiv.) and 2-(1H-benzotriazol-1-yl)-1,1,3,3-tetramethyluroniumtetrafluoroborate (TBTU, 44.90 g, 0.140 mol, 1.1 equiv.). After stirring the resulting thin white suspension for two days, the reaction is quenched by adding water (200 ml) and the two phases separated. The organic phase is back-extracted twice with dichloromethane (100 ml). The combined organic phases are washed with an aqueous 1M HCl solution (150 ml) and brine (100 ml), dried with sodium sulfate, filtered and concentrated under reduced pressure to a light yellow oil. The crude product was recrystallized in tert-butyl methyl ether (300 ml). The filtrate was purified by flash chromatography eluting with 30% ethyl acetate in hexanes and recrystallized in a (10:90) ethyl acetate:hexanes mixture. The white solid products were combined (47.28 g, 78%)

Scheme 2
Palladium catalyzed coupling and deprotection to Intermediate 8

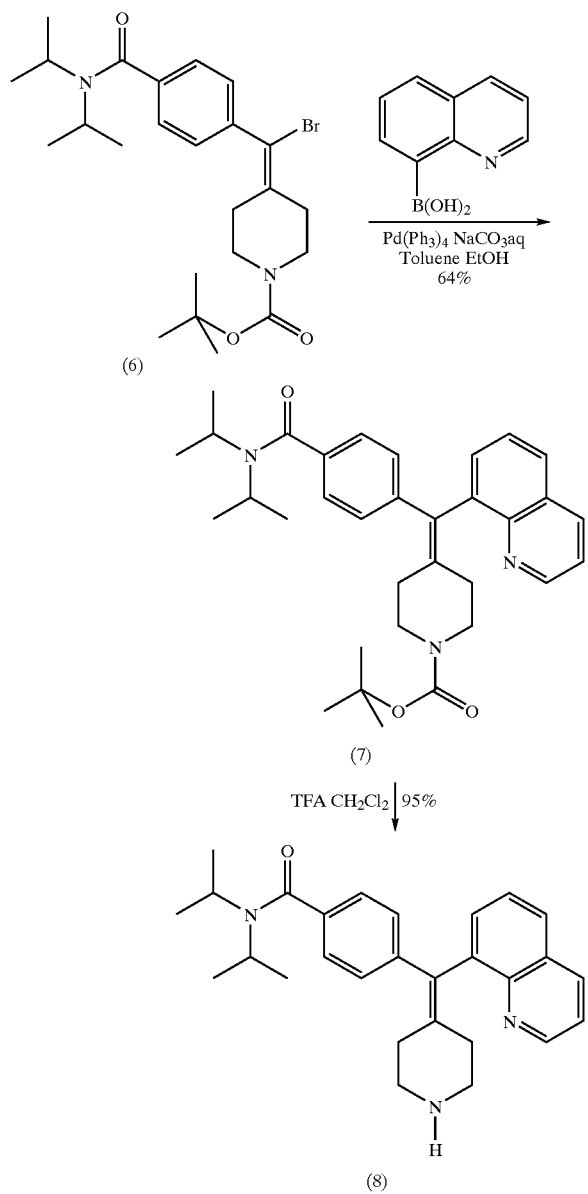

Intermediate 7: 4-[1-(4-Diisopropylcarbamoyl-phenyl)-1-quinolin-8-yl-methylene]-piperidine-1-carboxylic acid tert-butyl ester To a solution of bromide (6) (10.75 g, 22.47 mmol, 1.0 equiv.) in toluene (150 ml) at room temperature was added 8-quinolineboronic acid (4.66 g, 26.92 mmol, 1.2 equiv.) followed by ethanol (30 ml) and sodium carbonate (2M aqueous solution, 28.1 ml, 56.18 mmol, 2.5 equiv.). After purging with nitrogen the system for 15 minutes, tetrakis (triphenylphopshine)palladium(0) (1.87 g, 1.62 mmol, 0.072 equiv.) was added to the mixture which was then brought to 90° C. After stirring overnight, the reaction was cooled down to room-temperature, quenched with water (100 ml) and the phases separated. The organic phase was washed with water (100 ml) and then with brine (50 ml), dried with sodium sulfate, filtered and concentrated under reduced pressure. The crude product was purified by flash chromatography eluting with 50% ethyl acetate in hexanes (7.57 g, 64%).

Intermediate 8: N,N-Diisopropyl-4-(1-piperidin-4-ylidene-1-quinolin-8-yl-methyl)-benzamide To a solution of the carbamate (7) (7.57 g, 14.34 mmol, 1.0 equiv.) in dichoromethane (120 ml) at room temperature was added trifluoroacetic acid (TFA) (11.05 ml, 143.4 mmol, 10.0 equiv.). After stirring for 2.5 hours, the reaction was quenched by the addition of a 2M aqueous sodium hydroxide solution (80 ml). The phases were separated. The acqueous phase was back-extracted three times with dichloromethane (50 ml). The organic phases were combined, dried with sodium sulfate, filtered and concentrated under reduced pressure to provide 5.84 g of desired compound (95%).

A aliquot (375 mg, 0.88 mmol) of the deprotected amine was purified by flash chromatography eluting with 5% methanol in dichloromethane. The fraction was concentrated under reduced pressure and diluted in diethyl ether and dichloromethane. To this mixture was added 1M HCl solution in diethyl ether (4 ml, ca. 3.5 equiv.). The resulting mixture was then concentrated under reduced pressure. The white solids were triturated with diethyl ether and concentrated under reduced pressure to yield 350 mg of Intermediate (8) as the hydrochloride salt.

Examples 1–12 were synthesized following the general synthetic procedure depicted below.

Scheme 3
Reductive amination of Intermediate 8 to give compounds of the present invention

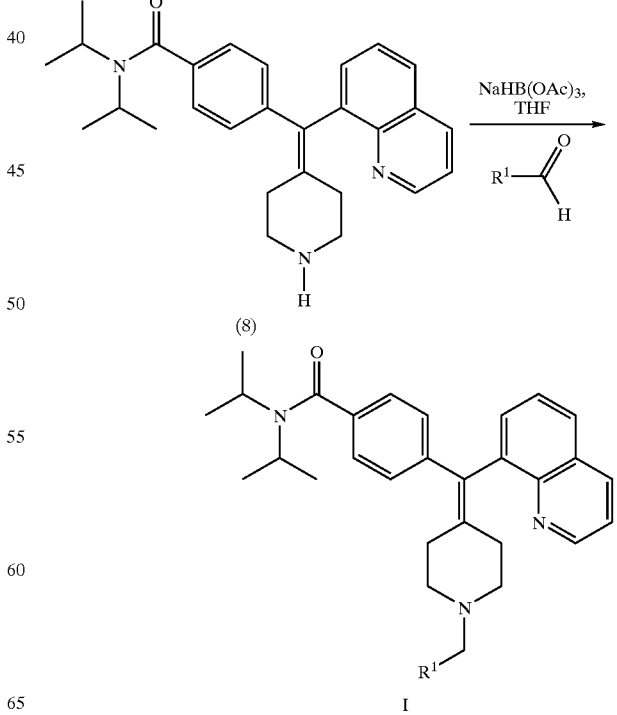

The synthesis of Example 1, below is typical.

Scheme 4
Reductive amination of Intermediate 8 and benzaldehyde to give Example 1

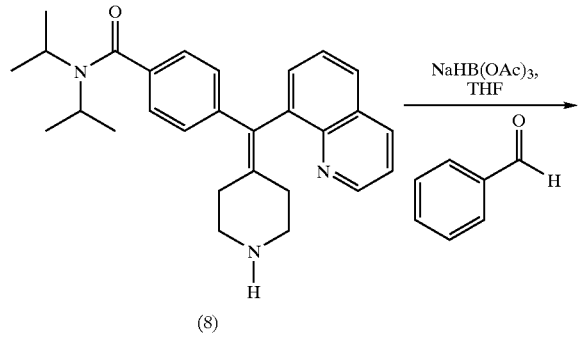

(8)

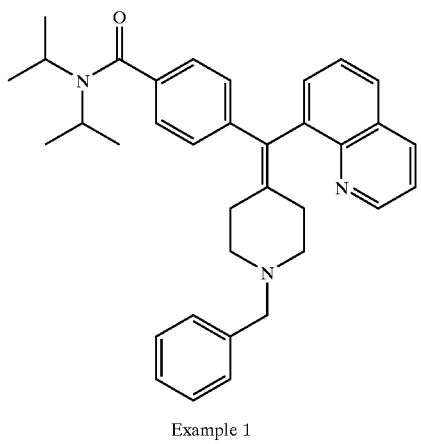

Example 1

Example 1

4-[1-(1-Benzyl-piperidin-4-ylidene)-1-quinolin-8-yl-methyl]-N,N-diisopropyl-benzamide To a solution of amine (8) (451 mg, 1.05 mmol, 1.0 equiv.) in tetrahydrofuran (20 ml) at room temperature was added benzaldehyde (129 μl, 1.27 mmol, 1.2 equiv.). After stirring for 10 minutes sodium triacetoxyborohydride (292 mg, 1.38 mmol, 1.3 equiv.) was added to the solution. After stirring overnight, the reaction mixture was diluted with dichloromethane (10 ml) and 2M aqueous sodium hydroxide solution (15 ml). The phases were separated and the organic phase washed with brine (15 ml). The former aqueous phase is back-extracted with dichloromethane three times (15 ml). The organic phases were combined, dried with sodium sulfate, filtered and concentrated under reduced pressure. The crude product was purified by flash chromatography eluting with 5% methanol in dichloromethane. The fraction was concentrated under reduced pressure and diluted in diethyl ether and dichloromethane. To this mixture was added 1M HCl solution in diethyl ether (4 ml, ca. 3.5 equiv.). The resulting mixture was then concentrated under reduced pressure. The white solids were triturated with diethyl ether and concentrated under reduced pressure to yield Example 1 (283 mg, 41%).

$^1$H NMR (δ in ppm): (400 MHz, DMSO) 9.01 (m, 1H, Ar—H); 8.65 (m, 1H, Ar—H); 8.05 (br s, 1H, Ar—H); 7.72 (m, 3H, Ar—H); 7.54 (br s, 2H, Ar—H); 7.39 (s, 3H, Ar—H); 7.34 (d, J=7.4 Hz, 2H, Ar—H); 7.15 (m, 2H, Ar—H); 4.25 (m, 2H, NCH$_2$Ar); 3.55 (br s, 1H, NCH); 3.40 (m, 2H, CH$_2$); 3.20 (m, 1H, CH$_2$); 3.03 (m, 2H, CH$_2$, NCH$_2$); 2,72 (m, 2H, NCH$_2$); 2.41 (m, 2H, NCH$_2$); 1.16 (m, 12H, CH$_3$)

Elemental analysis: Found C, 62.95; H, 7.08; N, 6.19. Calculated for C$_{35}$H$_{39}$N$_3$O×2.9HCl×2.5H$_2$O C, 62.89; H, 7.07; N, 6.29%.

Examples 2–12 were prepared analogously. Analytical data for Examples 1–12 are in Table 1 below.

TABLE 1

Analytical Data, for Compounds of the Present Invention.

| Ex. # | R$^1$ | Name | NMR data (400 MHz) |
|---|---|---|---|
| 1 | (phenyl) | 4-[1-(1-Benzyl-piperdin-4-ylidene)-1-quinolin-8-yl-methyl]-N,N-diisopropyl-benzamide. | (400 MHz, DMSO), 9.01 (m, 1H, Ar-H); 8.65 (m, 1H, Ar-H); 8.05 (br s, 1H, Ar-H); 7.72 (m, 3H, Ar-H); 7.54 (br s, 2H, Ar-H); 7.39 (s, 3H, Ar-H); 7.34 (d, J = 7.4 Hz, 2H, Ar-H); 7.15 (m, 2H, Ar-H); 4.25 (m, 2H, NCH$_2$Ar); 3.55 (br s, 1H, NCH); 3.40 (m, 2H, CH$_2$); 3.20 (m, 1H, CH$_2$); 3.03 (m, 2H, CH$_2$, NCH$_2$); 2.72 (m, 2H, NCH$_2$); 2.41 (m, 2H, NCH2); 1.16 (m, 12H, CH$_3$) |
| 2 | (pyridin-2-yl) | N,N-Diisopropyl-4-[1-(1-pyridin-2-ylmethyl-piperidin-4-ylidene)-1-quinolin-8-yl-methyl]-benzamide. | (400 MHz, DMSO) 9.15 (m, 1H, Ar-H); 8.90 (m, 1H, Ar-H); 8.62 (d, J = 4.6 Hz, 1H, Ar-H); 8.17 (m, 1H, Ar-H); 7.87 (m, 4H, Ar-H); 7.65 (m, 1H, Ar-H); 7.43 (m, 3H, Ar-H); 7.16 (d, J = 7.4 Hz, 2H, Ar-H); 4.43 (s, 2H, NCH$_2$Ar); 3.55 (br s, 3H, NCH, CH$_2$); 3.33 (m, 2H, CH$_2$); 3.14 (br s, 1H, CH$_2$); 2.73 (m, 2H, NCH$_2$); 2.20 (m, 2H, NCH$_2$); 1.11 (br s, 12H, CH$_3$) |

TABLE 1-continued

Analytical Data, for Compounds of the Present Invention.

| Ex. # | R¹ | Name | NMR data (400 MHz) |
|---|---|---|---|
| 3 | 4-pyridyl | N,N-Diisopropyl-4-[1-(1-pyridin-4-ylmethyl-piperidin-4-ylidene)-1-quinolin-8-yl-methyl]-benzamide. | (400 MHz, DMSO) 8.96 (m, 1H, Ar-H); 8.78 (m, 2H, Ar-H); 8.50 (s, 1H, Ar-H); 7.98 (br s, 1H, Ar-H); 7.89 (br s, 2H, Ar-H); 7.64 (m, 3H, Ar-H); 7.30 (d, J = 8.8 Hz, 2H, Ar-H); 7.15 (d, J = 7.4 Hz, 2H, Ar-H); 4.44 (m, 2H, NCH$_2$Ar); 3.55 (br s, 2H, NCH); 3.41 (br s, 1H, CH$_2$); 3.25 (br s, 1H, CH$_2$); 3.04 (m, 2H, CH$_2$); 2.70 (m, 2H, NCH$_2$); 2.40 (m, 2H, NCH$_2$); 1.16 (br s, 12H, CH$_3$) |
| 4 | thiophen-2-yl | N,N-Diisopropyl-4-[1-quinolin-8-yl-1-(1-thiophen-2-ylmethyl-piperidin-4-ylidene)-methyl]-benzamide. | 9.00 (br s, 1H, Ar-H); 8.26 (br s, 1H, Ar-H); 8.03 (m, 1H, Ar-H); 7.65 (m, 4H, Ar-H); 7.30 (m, 3H, Ar-H); 7.16 (m, 2H, Ar-H); 7.10 (m, 1H, Ar-H); 4.52 (m, 2H, NCH$_2$Ar); 3.50 (m, 3H, NCH, CH$_2$); 3.21 (m, 2H, CH$_2$); 3.04 (br s, 1H, CH$_2$); 2.70 (m, 2H, NCH$_2$); 2.36 (m, 1H, NCH$_2$); 1.98 (m, 1H, NCH$_2$); 1.14 (br s, 12H, CH$_3$) |
| 5 | thiophen-3-yl | N,N-Diisopropyl-4-[1-quinolin-8-yl-1-(1-thiophen-2-ylmethyl-piperidin-4-ylidene)-methyl]-benzamide. | 8.95 (s, 1H, Ar-H); 8.53 (br s, 1H, Ar-H); 7.99 (br s, 1H, Ar-H); 7.71 (m, 5H, Ar-H); 7.28 (m, 3H, Ar-H); 7.15 (dd, J = 4.6, 8.3 Hz, 2H, Ar-H); 4.30 (s, 2H, NCH$_2$Ar); 3.54 (br s, 2H, NCH); 3.44 (m, 1H, CH$_2$); 3.22 (m, 1H, CH$_2$); 2.97 (m, 2H, CH$_2$); 2.68 (m, 2H, NCH$_2$); 2.36 (m, 1H, NCH$_2$); 1.93 (m, 1H, NCH$_2$); 1.14 (m, 12H, CH$_3$) |
| 6 | furan-3-yl | N,N-Diisopropyl-4-[1-quinolin-8-yl-1-(1-furan-3-ylmethyl-piperidin-4-ylidene)-methyl]-benzamide. | 8.99 (s, 1H, Ar-H); 8.59 (br s, 1H, Ar-H); 8.01 (br s, 1H, Ar-H); 7.81 (s, 1H, Ar-H); 7.71 (m, 4H, Ar-H); 7.32 (m, 2H, Ar-H); 7.15 (m, 2H, Ar-H); 6.70 (s, 1H, Ar-H); 4.15 (s, 2H, NCH$_2$Ar); 3.56 (br s, 2H, NCH); 3.43 (m, 1H, CH$_2$); 3.25 (m, 1H, CH$_2$); 2.98 (m, 2H, CH$_2$); 2.68 (m, 2H, NCH$_2$); 2.38 (m, 1H, NCH$_2$); 1.97 (m, 1H, NCH$_2$); 1.19 (m, 12H, CH$_3$) |
| 7 | furan-2-yl | N,N-Diisopropyl-4-[1-quinolin-8-yl-1-(1-furan-2-ylmethyl-piperidin-4-ylidene)-methyl]-benzamide. | 8.98 (s, 1H, Ar-H); 8.51 (br s, 1H, Ar-H); 8.01 (br s, 1H, Ar-H); 7.78 (s, 1H, Ar-H); 7.70 (m, 3H, Ar-H); 7.32 (m, 2H, Ar-H); 7.16 (m, 2H, Ar-H); 6.69 (s, 1H, Ar-H); 6.53 (s, 1H, Ar-H); 4.31 (s, 2H, NCH$_2$Ar); 3.55 (m, 3H, NCH, CH$_2$); 3.22 (m, 2H, CH$_2$); 3.00 (m, 1H, CH$_2$); 2.68 (m, 2H, NCH$_2$); 2.38 (m, 1H, NCH$_2$); 1.95 (m, 1H, NCH$_2$); 1.16 (m, 12H, CH$_3$) |
| 8 | 4-methoxyphenyl | N,N-Diisopropyl-4-{1-[1-(4-methoxy-benzyl)-piperidin-4-ylidene]-1-quinolin-8-yl-methyl}-benzamide. | (400 MHz, DMSO) 9.09 (m, 1H, Ar-H); 8.76 (m, 1H, Ar-H); 8.10 (br s, 1H, Ar-H); 7.77 (m, 3H, Ar-H); 7.47 (m, 2H, Ar-H); 7.36 (m, 2H, Ar-H); 7.16 (m, 2H, Ar-H); 6.93 (d, J = 8.4 Hz, 2H, Ar-H); 4.18 (s, 2H, NCH$_2$Ar); 3.71 (s, 3H, OMe); 3.53 (br s, 2H, NCH); 3.40 (m, 1H, CH$_2$); 3.20 (br s, 1H, CH$_2$); 3.11 (m, 2H, CH$_2$); 2.70 (m, 2H, NCH$_2$); 2.40 (m, 1H, NCH$_2$); 1.95 (m, 1H, NCH$_2$); 1.81 (br s, 12H, CH$_3$) |
| 9 | thiazol-2-yl | N,N-Diisopropyl-4-[1-quinolin-8-yl-1-(1-thiazol-2-ylmethyl-piperidin-4-ylidene)-methyl]-benzamide. | (400 MHz, DMSO) 9.03 (br s, 1H, Ar-H); 8.67 (br s, 1H, Ar-H); 8.06 (br s, 1H, Ar-H); 7.90 (m, 2H, Ar-H); 7.73 (br s, 3H, Ar-H); 7.34 (br s, 2H, Ar-H); 7.15 (d, J = 8.4 Hz, 2H, Ar-H); 4.72 (m, 2H, NCH$_2$Ar); 3.55 (br s, 2H, NCH); 3.20 (m, 4H, CH$_2$); 2.70 (m, 2H, NCH$_2$); 2.40 (m, 1H, NCH$_2$); 2.00 (m, 1H, NCH$_2$); 1.16 (br s, 12H, CH$_3$) |
| 10 | 1H-imidazol-2-yl | 4-{1-[1-(1H-Imidazol-2-ylmethyl)-piperidin-4-ylidene]-1-quinolin-8-yl-methyl}-N,N-diisopropylbenzamide. | (400 MHz, DMSO) 9.02 (br s, 1H, Ar-H); 8.63 (br s, 1H, Ar-H); 8.05 (br s, 1H, Ar-H); 7.71 (m, 5H, Ar-H); 7.35 (br s, 2H, Ar-H); 7.15 (d, J = 8.3 Hz, 2H, Ar-H); 4.54 (s, 2H, NCH$_2$Ar); 3.54 (br s, 2H, NCH); 3.24 (m, 4H, CH$_2$); 2.70 (m, 2H, NCH$_2$); 2.14 (m, 2H, NCH$_2$); 1.24 (br s, 12H, CH3) |

TABLE 1-continued

Analytical Data, for Compounds of the Present Invention.

| Ex. # | R¹ | Name | NMR data (400 MHz) |
|---|---|---|---|
| 11 | 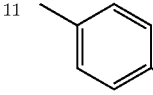 | N,N-Diisopropyl-4-(1-[1-(4-bromo-benzyl)-piperidin-4-ylidene]-1-quinolin-8-yl-methyl9-benzamide. | (400 MHz, DMSO) 8.97 (br s, 1H, Ar-H); 8.56 (m, 1H, Ar-H); 8.00 (br s, 1H, Ar-H); 7.60 (m, 5H, Ar-H); 7.49 (m, 2H, Ar-H); 7.30 (m, 2H, Ar-H); 7.15 (m, 2H, Ar-H); 4.27 (s, 2H, NCH$_2$Ar); 3.55 (br s, 2H, NCH); 3.40 (m, 2H, CH$_2$); 3.21 (br s, 1H, CH$_2$); 2.95 (m, 2H, CH$_2$, NCH$_2$); 2.70 (m, 2H, NCH$_2$); 2.36 (m, 1H, NCH$_2$); 1.11 (br s, 12H, CH$_3$) |
| 12 | 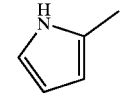 | N,N-Diisopropyl-4-[1-quinolin-8-yl-1-(1-pyrrol-2-ylmethyl-piperidin-4-ylidene)-methyl]-benzamide. | |

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Salts include, but are not limited to, pharmaceutically acceptable salts. Examples of pharmaceutically acceptable salts within the scope of the present invention include: acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate. Examples of pharmaceutically unacceptable salts within the scope of the present invention include: hydroiodide, perchlorate, and tetrafluoroborate. Pharmaceutically unacceptable salts could be of use because of their advantageous physical and/or chemical properties, such as crystallinity.

Preferred pharmaceutically acceptable salts are the hydrochlorides, sulfates and bitartrates. The hydrochloride and sulfate salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration. Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

BIOLOGICAL EVALUATION

In vitro Model

Cell Culture

A. Human 293S cells expressing cloned human μ, δ, and κ receptors and neomycin resistance were grown in suspension at 37° C. and 5% $CO_2$ in shaker flasks containing calcium-free DMEM10% FBS, 5% BCS, 0.1% Pluronic F-68, and 600 μg/ml geneticin.

B. Mouse and rat brains were weighed and rinsed in ice-cold PBS (containing 2.5 mM EDTA, pH 7.4). The brains were homogenized with a polytron for 15 sec (mouse) or 30 sec (rat) in ice-cold lysis buffer (50 mM Tris, pH 7.0, 2.5 mM EDTA, with phenylmethylsulfonyl fluoride added just prior use to 0.5 MmM from a 0.5M stock in DMSO:ethanol).

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with sodium dodecyl sulfate.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 μg/ml aprotinin, 10 μM bestatin, 10 μM diprotin A, no DTT). Aliquots of 100 μl were added to iced 12×75 mm polypropylene tubes containing 100 μl of the appropriate radioligand and 100 μl of test compound at various concentrations. Total (TB) and nonspecific (NS) binding were determined in the absence and presence of 10 μM naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 μl MS-20 scintillation fluid/well.

Functional Assays

The agonist activity of the compounds is measured by determining the degree to which the compounds receptor complex activates the binding of GTP to G-proteins to which the receptors are coupled. In the GTP binding assay, GTP $[\gamma]^{35}S$ is combined with test compounds and membranes from HEK-293S cells expressing the cloned human opioid receptors or from homogenised rat and mouse brain. Agonists stimulate $GTP[\gamma]^{35}S$ binding in these membranes. The $EC_{50}$ and $E_{max}$ values of compounds are determined from dose-response curves. Right shifts of the dose response curve by the delta antagonist naltrindole are performed to verify that agonist activity is mediated through delta receptors.

Procedure for Rat Brain GTP

Rat brain membranes are thawed at 37° C., passed 3 times through a 25-gauge blunt-end needle and diluted in the GTPγS binding (50 mM Hepes, 20 mM NaOH, 100 mM NaCl, 1 mM EDTA, 5 mM $MgCl_2$, pH 7.4, Add fresh: 1 mM DTT, 0.1% BSA). 120 μM GDP final is added membranes dilutions. The EC50 and Emax of compounds are evaluated from 10-point dose-response curves done in 300 μl with the appropriate amount of membrane protein (20 μg/well) and 100000–130000 dpm of $GTP\gamma^{35}S$ per well (0.11–0.14 nM). The basal and maximal stimulated binding are determined in absence and presence of 3 μM SNC-80

Data Analysis

The specific binding (SB) was calculated as TB-NS, and the SB in the presence of various test compounds was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves. Biological activity of the compounds of the present invention is indicated in Table 2.

TABLE 2

| | Biological data. | | | | | | |
|---|---|---|---|---|---|---|---|
| | HDELTA (nM) | | | RAT BRAIN (nM) | | MOUSE BRAIN (nM) | |
| Ex. # | $IC_{50}$ | $EC_{50}$ | % EMax | $EC_{50}$ | % EMax | $EC_{50}$ | % EMax |
| 1-11 | 0.78–5 | 0.53–11.96 | 96–102 | 4.68–65.4 | 97–144 | 7.09–88.4 | 100–151 |

Receptor Saturation Experiments

Radioligand $K_\delta$ values were determined by performing the binding assays on cell membranes with the appropriate radioligands at concentrations ranging from 0.2 to 5 times the estimated $K_\delta$ (up to 10 times if amounts of radioligand required are feasible). The specific radioligand binding was expressed as pmole/mg membrane protein. Values of $K_\delta$ and $B_{max}$ from individual experiments were obtained from non-linear fits of specifically bound (B) vs. nM free (F) radioligand from individual according to a one-site model.

Determination Of Mechano-Allodynia Using Von Frey Testing

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \ g \ threshold = 10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \ MPE = \frac{\text{Drug treated threshold (g)} - \text{allodynia threshold (g)} \times 100}{\text{Control threshold (g)} - \text{allodynia threshold (g)}}$$

Administration of Test Substance

Rats were injected (subcutaneously, intraperitoneally, intravenously or orally) with a test substance prior to von Frey testing, the time between administration of test compound and the von Frey test varied depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1–100 μmol/kg.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

For the anxiety and anxiety-like indications, efficacy has been established in the geller-seifter conflict test in the rat.

For the functional gastrointestina disorder indication, efficacy can be established in the assay described by Coutinho S V et al, in American Journal of Physiology—Gastrointestinal & Liver Physiology. 282(2):G307–16, 2002 February, in the rat.

What is claimed is:

1. A compound of the formula I

I wherein $R^1$ is selected from any one of (i) phenyl;

(ii) pyridinyl

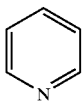

(iii) thienyl

(iv) furanyl

(v) imidazolyl

(vi) triazolyl

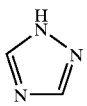

(vii) pyrrolyl

(viii) thiazolyl

, (ix) pyridyl-N-oxide

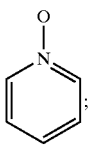;

where each $R^1$ phenyl ring and $R^1$ heteroaromatic ring may independently be further substituted by 1, 2 or 3 substituents independently selected from straight and branched $C_1$–$C_6$ alkyl, $NO_2$, $CF_3$, $C_1$–$C_6$ alkoxy, chloro, fluoro, bromo, and iodo;
as well as salts thereof.

2. A compound according to claim 1, wherein each $R^1$ phenyl ring and $R^1$ heteroaromatic ring may optionally and independently be further substituted by 1, 2 or 3 substituents independently selected from methyl, $CF_3$, chloro, fluoro, bromo, and iodo.

3. A compound according to claim 1, wherein each $R^1$ phenyl ring and $R^1$ heteroaromatic ring may independently be further substituted by a methyl group.

4. A compound according to claim 1, wherein $R^1$ is phenyl, pyrrolyl, pyridinyl, thienyl or furanyl.

5. A compound according to claim 1 or 2, selected from any one of

4-[1-(1-Benzyl-piperidin-4-ylidene)-1-quinolin-8-yl-methyl]-N,N-diisopropyl-benzamide; N,N-Diisopropyl-4-[1-(1-pyridin-2-ylmethyl-piperidin-4-ylidene)-1-quinolin-8-yl-methyl]-benzamide, N,N-Diisopropyl-4-[1-(1-pyridin-4-ylmethyl-piperidin-4-ylidene)-1-quinolin-8-yl-methyl]-benzamide, N,N-Diisopropyl-4-[1-quinolin-8-yl-1-(1-thiophen-2-ylmethyl-piperidin-4-ylidene)-methyl]-benzamide, N,N-Diisopropyl-4-[1-quinolin-8-yl-1-(1-thiophen-3-ylmethyl-piperidin-4-ylidene)-methyl]-benzamide, N,N-Diisopropyl-4-[1-quinolin-8-yl-1-(1-furan-3-ylmethyl-piperidin-4-ylidene)-methyl]-benzamide, N,N-Diisopropyl-4-[1-quinolin-8-yl-1-(1-furan-2-ylmethyl-piperidin-4-ylidene)-methyl]-benzamide, N,N-Diisopropyl-4-[1-quinolin-8-yl-1-(1-pyrrol-2-ylmethyl-piperidin-4-ylidene)-methyl]-benzamide, N,N-Diisopropyl-4-{1-[1-(4-bromo-benzyl)-piperidin-4-ylidene]-1-quinolin-8-yl-methyl}-benzamide, 4-{1-[1-(1H-Imidazol-2-ylmethyl)-piperidin-4-ylidene]-1-quinolin-8-yl-methyl}-N,N-diisopropylbenzamide, N,N-Diisopropyl-4-{1-[1-(4-methoxy-benzyl)-piperidin-4-ylidene]-1-quinolin-8-yl-methyl}-benzamide, and N,N-Diisopropyl-4-[1-quinolin-8-yl-1-(1-thiazol-2-ylmethyl-piperidin-4-ylidene)-methyl]-benzamide.

6. A compound according to any of the preceding claims, in form of its hydrochloride, dihydrochloride, sulfate, tartrate, ditrifluoroacetate or citrate salts.

7. A pharmaceutical composition comprising a compound of the formula I according to claim 1 as an active ingredient, together with a pharmaceutically acceptable carrier.

8. A method for the treatment of pain, whereby an effective amount of a compound of the formula I according to claim 1 is administered to a subject in need of pain management.

9. A method for the treatment of functional gastrointestinal disorders, whereby an effective amount of a compound of the formula I according to claim 1, is administered to a subject suffering from said functional gastrointestinal disorder.

10. A method for the treatment of anxiety, whereby an effective amount of a compound of the formula I according to claim 1, is administered to a subject suffering from said anxiety.

11. A process for preparing a compound of formula I, comprising the reaction of, A) reacting a compound of the general formula II

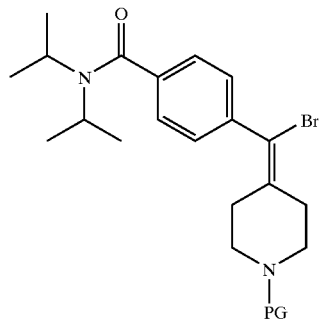

wherein PG is a urethane protecting group such as Boc or CBZ, or a benzyl or a substituted benzyl protecting group, such as 2,4-dimethoxybenzyl, with 8-quinoline boronic acid, using a palladium catalyst, e.g. Pd(PPh$_3$)$_4$, in the presence of a base, e.g. Na$_2$CO$_3$, to give the compounds of general formula III,

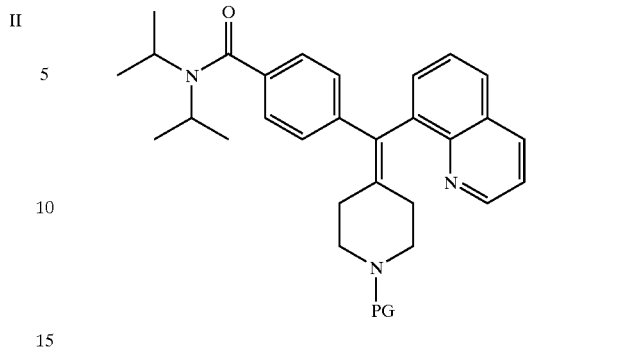

which is thereafter deprotected, under standard conditions and alkylated under reductive conditions with a compound of the general formula R$^1$—CHO to give compounds of the general formula I.

* * * * *